(12) United States Patent
Wang et al.

(10) Patent No.: US 12,377,089 B2
(45) Date of Patent: Aug. 5, 2025

(54) QUINOLINE DERIVATIVE USED FOR SOFT TISSUE SARCOMA COMBINATION THERAPY

(71) Applicant: CHIA TAI TIANQING PHARMACEUTICAL GROUP CO., LTD., Lianyungang (CN)

(72) Inventors: Zhiming Wang, Shanghai (CN); Shilong Zhang, Shanghai (CN); Rongyuan Zhuang, Shanghai (CN); Xi Guo, Shanghai (CN); Yan Wang, Shanghai (CN); Hua Yang, Shanghai (CN); Weiqi Lu, Shanghai (CN); Yuhong Zhou, Shanghai (CN); Lei Gao, Lianyungang (CN)

(73) Assignee: Chia Tai Tianqing Pharmaceutical Group Co., Ltd., Lianyungang (CN)

( * ) Notice: Subject to any disclaimer, the term of this patent is extended or adjusted under 35 U.S.C. 154(b) by 842 days.

(21) Appl. No.: 17/609,990

(22) PCT Filed: May 11, 2020

(86) PCT No.: PCT/CN2020/089545
§ 371 (c)(1),
(2) Date: Nov. 9, 2021

(87) PCT Pub. No.: WO2020/228656
PCT Pub. Date: Nov. 19, 2020

(65) Prior Publication Data
US 2022/0211693 A1   Jul. 7, 2022

(30) Foreign Application Priority Data
May 10, 2019 (CN) .......................... 201910390149.8

(51) Int. Cl.
*A61K 31/4709* (2006.01)
*A61K 31/704* (2006.01)
*A61K 45/06* (2006.01)
*A61P 35/00* (2006.01)

(52) U.S. Cl.
CPC ........ *A61K 31/4709* (2013.01); *A61K 31/704* (2013.01); *A61K 45/06* (2013.01); *A61P 35/00* (2018.01)

(58) Field of Classification Search
CPC .. A61K 31/4709; A61K 31/704; A61K 45/06; A61K 2300/00; A61P 35/00
USPC ......................................................... 514/34
See application file for complete search history.

(56) References Cited

U.S. PATENT DOCUMENTS

| | | | |
|---|---|---|---|
| 9,968,597 B2 * | 5/2018 | Zhang | ................ A61K 31/4709 |
| 10,544,125 B2 | 1/2020 | Chen et al. | |
| 2016/0193347 A1 | 7/2016 | Xu | |
| 2016/0326138 A1 | 11/2016 | Chen | |
| 2017/0202828 A1 | 7/2017 | Zhang | |
| 2019/0125739 A1 | 5/2019 | Chen | |

FOREIGN PATENT DOCUMENTS

| | | | | |
|---|---|---|---|---|
| CA | 2951061 A1 | 12/2015 | | |
| CA | 2984444 A1 | 11/2016 | | |
| CA | 3137204 A1 | 10/2020 | | |
| CN | 105311029 | * 2/2016 | ......... A61K 31/4709 | |
| CN | 105311029 A | 2/2016 | | |
| CN | 107296811 A | 10/2017 | | |
| CN | 107771078 A | 3/2018 | | |
| CN | 107970241 A | 5/2018 | | |
| EP | 3 153 169 A1 | 4/2017 | | |
| JP | 2016527192 A | 9/2016 | | |
| WO | WO 2016/179123 A1 * | 11/2016 | ......... A61K 31/4709 | |
| WO | WO2018214925 A1 * | 11/2018 | .............. A61P 35/00 | |

OTHER PUBLICATIONS

Jelic et al, European Journal of Cancer, 1997, 33(2), 220-225.*
Cao et al, Asian Pac J Cancer Prev, 2013, 14, (12), 7171-7177.*
Zhi-ming Wang et al, American Association for Cancer Research, 2022, 28, 5290-96.*
Shenglong, Li et al., "Anlotinib Hydrochloride Combined With Epirubicin and Ifosfamide for Soft Tissue Sarcoma Patients (ALTER-S005)," ClinicalTrials.gov NCT03815474, Jan. 24, 2019.
Wei, Guowen et al., "Anlotinib Hydrochloride Combined With Liposomal Doxorubicin in the Treatment of Locally Advanced or Metastatic Soft Tissue Sarcoma (ALTER-S001)," ClinicalTrials.gov NCT03880695, Mar. 19, 2019.
Extended European Search Report, European Patent Application 20805847.9, Dec. 16, 2022, 10 pages.
Jelic, S. et al., "Randomised Study of High-dose Epirubicin Versus High-dose Epirubicin-Cisplatin Chemotherapy for Advanced Soft Tissue Sarcoma", European Journal of Cancer, Elsevier, Amsterdam, NL, vol. 33, No. 2, Feb. 1, 1997, pp. 220-225, XP004282502, ISSN: 0959-8049, DOI: 10,1016/S0959-8049 (96) 00297-3.

(Continued)

*Primary Examiner* — Ganapathy Krishnan
(74) *Attorney, Agent, or Firm* — NIXON PEABODY LLP

(57) ABSTRACT

A quinoline derivative used for soft tissue sarcoma combination therapy, relating to a use of the quinoline derivative in combination with a second therapeutic drug to treat soft tissue sarcoma, wherein the second therapeutic drug may be a chemotherapy drug, a small molecule targeted anti-tumour drug or an immunotherapy drug. The chemical name of the quinoline derivative compound I is 1-[[[4-(4-fluoro-2-methyl-1H-indol-5-yl)oxy-6-methoxyquinolin-7-yl]oxy]methyl]cyclopropylamine.

10 Claims, No Drawings

(56) References Cited

OTHER PUBLICATIONS

Liu, Wenshuai et al., "Advances of Systemic Treatment For Adult Soft-Tissue Sarcoma", Chinese Clinical Oncology, vol. 7, No. 4, Aug. 1, 2008, pp. 1-13, XP093004711, ISSN: 2304-3865, DOI: 10,21037/cco.2018.08.02.

Wang, Z-M et al., "Efficacy and Safety of Anlotinib, a Multikinase Angiogenesis Inhibitor, in Combination With Epirubicin in Preclinical Models of Soft Tissue Sarcoma," Cancer Med., 9(10): 3344-3352, Mar. 17, 2020.

International Search Report in International Application No. PCT/CN2020/089545, mailed Aug. 12, 2020 (10 pages).

Chi et al., "Safety and Efficacy of Anlotinib, a Multikinase Angiogenesis Inhibitor, in Patients with Refractory Metastatic Soft-Tissue Sarcoma", Clin Cancer Res, 24(21), pp. 5233-5238, Nov. 1, 2018 (Nov. 1, 2018).

* cited by examiner

QUINOLINE DERIVATIVE USED FOR SOFT TISSUE SARCOMA COMBINATION THERAPY

CROSS-REFERENCE TO RELATED APPLICATIONS

The present application is a U.S. National Stage Entry of International Application No. PCT/CN2020/089545 filed on May 11, 2020, which claims priority and benefit to Chinese Patent Application No. 201910390149.8, filed with National Intellectual Property Administration, PRC on May 10, 2019, each of which is hereby incorporated by reference in its entirety.

TECHNICAL FIELD

The present application belongs to the technical field of medicines and relates to a quinoline derivative for use in combination therapy of a soft tissue sarcoma. Specifically, the present application relates to use of the quinoline derivative for treating a soft tissue sarcoma in combination with a second therapeutic drug, wherein the second therapeutic drug can be a chemotherapeutic drug, a small molecule targeted anti-tumor drug or an immunotherapeutic drug.

BACKGROUND

A soft tissue sarcoma (STS) is a malignant tumor that is derived from mesenchymal tissues and epiblast nervous tissues interwoven therewith, including non-epithelial tissues except lymphohematopoietic tissues, i.e., fibers, fat, muscle, and mesothelium, as well as blood vessels, lymphatic vessels and peripheral nerves distributed therein. It is commonly located in the limbs, trunk and retroperitoneum, and makes up 1% of adult malignant tumors and 15% of children's tumors. It is mainly characterized by wide distribution and various types.

WHO classifies soft tissue sarcomas into more than 50 subtypes. The common subtypes include liposarcoma, leiomyosarcoma, angiosarcoma, synovial sarcoma, fibrosarcoma, pleomorphic undifferentiated sarcoma, malignant nerve sheath tumor, etc. As soft tissue sarcomas are highly malignant, the median survival time for patients is short.

WO2008112407 disclosed in Example 24 a quinoline derivative tyrosine kinase inhibitor 1-[[[4-(4-fluoro-2-methyl-1H-indol-5-yl)oxy-6-methoxyquinolin-7-yl]oxy]methyl]cyclopropylamine and a preparation method thereof, and the inhibitor has a structural formula as shown in formula I:

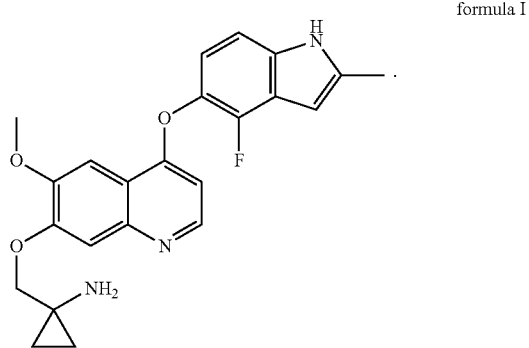 [SMILES: COc1cc2c(Oc3ccc4[nH]c(C)cc4c3F)ccnc2cc1OCC1(N)CC1]

formula I

SUMMARY

In one aspect, the present application provides a pharmaceutical combination for use in treating a soft tissue sarcoma, comprising (i) a compound of formula I or a pharmaceutically acceptable salt thereof; and (ii) at least one second therapeutic drug,

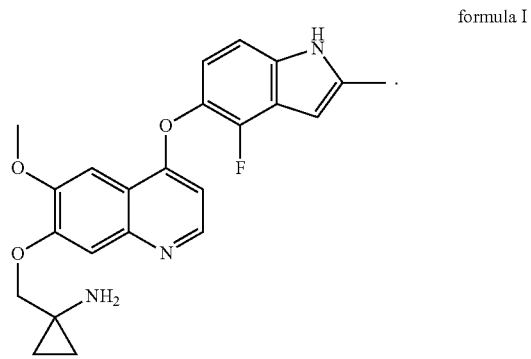 [SMILES: COc1cc2c(Oc3ccc4[nH]c(C)cc4c3F)ccnc2cc1OCC1(N)CC1]

formula I

In another aspect, the present application further provides use of the pharmaceutical combination for preparing a medicament for treating a soft tissue sarcoma.

In yet another aspect, the present application further provides a method for treating a soft tissue sarcoma, comprising administering to a subject in need thereof a therapeutically effective amount of the pharmaceutical combination disclosed herein. The pharmaceutical combination comprises (i) a compound of formula I or a pharmaceutically acceptable salt thereof; and (ii) at least one second therapeutic drug.

In one aspect, the present application provides a pharmaceutical combination for use in treating a soft tissue sarcoma, comprising (i) a compound of formula I or a pharmaceutically acceptable salt thereof; and (ii) at least one second therapeutic drug.

In some embodiments of the present application, the pharmaceutical combination comprises: (i) a pharmaceutical composition of the compound of formula I or the pharmaceutically acceptable salt thereof; and (ii) the at least one second therapeutic drug.

In some embodiments, the pharmaceutical combination comprises: (i) the compound of formula I or the pharmaceutically acceptable salt thereof; and (ii) at least one chemotherapeutic drug, optionally, the pharmaceutical combination is used in combination with radiation therapy. In some specific embodiments, provided is a pharmaceutical combination for use in treating a soft tissue sarcoma, comprising: (i) the compound of formula I or the pharmaceutically acceptable salt thereof; and (ii) epirubicin.

In some specific embodiments, the pharmaceutical combination comprises: (i) a pharmaceutical composition at a dose of 6 mg, 8 mg, 10 mg and/or 12 mg of the compound of formula I or the pharmaceutically acceptable salt thereof; and (ii) a pharmaceutical composition at a dose of 50-150 mg/m$^2$ epirubicin.

In some specific embodiments, the pharmaceutical combination comprises: (i) a pharmaceutical composition of the compound of formula I or the pharmaceutically acceptable salt thereof at a dose of 6 mg, 8 mg, 10 mg and/or 12 mg; and (ii) a pharmaceutical composition of epirubicin at a dose of 50, 54, 60, 72, 80, 90, 100, 110, 120, 135 and/or 150 mg/m$^2$.

In some embodiments, provided is a pharmaceutical combination for use in treating a soft tissue sarcoma, comprising (i) a pharmaceutical composition of the compound of formula I or the pharmaceutically acceptable salt thereof at a dose of 12 mg; and (ii) a pharmaceutical composition of epirubicin at a dose of 90 mg/m$^2$.

In another aspect, the present application provides use of the pharmaceutical combination for preparing a medicament for use in treating a soft tissue sarcoma, the pharmaceutical combination comprising: (i) a compound of formula I or a pharmaceutically acceptable salt thereof; and (ii) at least one second therapeutic drug, optionally, the pharmaceutical combination is used in combination with radiation therapy.

In yet another aspect, the present application provides a method for treating a soft tissue sarcoma, comprising: administering to a patient in need thereof a therapeutically effective amount of (i) the compound of formula I or the pharmaceutically acceptable salt thereof; and (ii) at least one second therapeutic drug.

The present application provides a method for treating an entity with a soft tissue sarcoma. In certain embodiments, the entity with a soft tissue sarcoma is, for example, a patient diagnosed with undifferentiated pleomorphic sarcoma or alveolar soft-part sarcoma. For example, in certain embodiments, the soft tissue sarcoma is a recurrent soft tissue sarcoma. In certain embodiments, the soft tissue sarcoma is a metastatic soft tissue sarcoma. In certain embodiments, the soft tissue sarcoma is a refractory soft tissue sarcoma. In certain embodiments, the soft tissue sarcoma is an unresectable soft tissue sarcoma. In some specific embodiments, the soft tissue sarcoma described herein is undifferentiated pleomorphic sarcoma. In some specific embodiments, the soft tissue sarcoma described herein is unresectable and/or metastatic undifferentiated pleomorphic sarcoma. In some other specific embodiments, the soft tissue sarcoma is alveolar soft-part sarcoma. In some specific embodiments, the soft tissue sarcoma described herein includes those specified in the 2013 World Health Organization (WHO) Classification, including but not limited to angiosarcoma, fibrosarcoma, leiomyosarcoma, liposarcoma, rhabdomyosarcoma, synovial sarcoma, dermatofibrosarcoma protuberan, malignant peripheral nerve sheath tumor, clear cell sarcoma, malignant mesenchymal sarcoma, epithelioid sarcoma, undifferentiated sarcoma, and gastrointestinal stromal tumor.

In some embodiments of the present application, the entity has previously received surgery, chemotherapy and/or radiation therapy. In some specific embodiments, the entity is one who has recurrent disease progression after achieving complete response following surgery, chemotherapy and/or radiation therapy. In some specific embodiments, the entity is one who has failed to achieve complete response or partial response following surgery, chemotherapy and/or radiation therapy.

In some embodiments of the present application, the entity has not previously been treated with systemic chemotherapy. In some embodiments, the entity has previously been treated with surgical treatment, radiation therapy, induction chemotherapy, concurrent chemotherapy and/or adjuvant chemotherapy. In some specific embodiments, the entity has not previously been treated with systemic chemotherapy, but has been treated with surgical treatment, radiation therapy, induction chemotherapy, concurrent chemotherapy and/or adjuvant chemotherapy. In some specific embodiments, the entity has recurrence of disease progression after achieving complete response following surgery, radiation therapy, induction chemotherapy, concurrent chemotherapy and/or adjuvant chemotherapy. In some specific embodiments, the entity has failed to achieve complete response or partial response following surgical treatment, radiation therapy, induction chemotherapy, concurrent chemotherapy and/or adjuvant chemotherapy. In some specific embodiments, the cancer metastasizes after the entity has been treated with surgery, radiation therapy, induction chemotherapy, concurrent chemotherapy and/or adjuvant chemotherapy.

In some embodiments of the present application, the soft tissue sarcoma includes a soft tissue sarcoma that has not previously been treated with anthracycline chemotherapy. In some embodiments, the anthracycline is, for example, one or more, such as one, two or three, of epirubicin, adriamycin, daunorubicin, pirarubicin, amrubicin, idarubicin, mitoxantrone, aclarubicin, valrubicin, zorubicin, pixantrone, or the like.

In some embodiments of the present application, for the use or methods for treatment, the second therapeutic drug can be administered once every week (q1w), every 2 weeks (q2w), every 3 weeks (q3w), or every 4 weeks (q4w). In a specific embodiment, epirubicin is administered once every 3 weeks.

The compound of formula I or the pharmaceutically acceptable salt thereof can be administered at a dose of 6 mg, 8 mg, 10 mg or 12 mg once daily according to an administration regimen of consecutively 2-week treatment and then 1-week interruption, and/or according to an administration regimen of consecutively 2-week treatment and then 2-week interruption.

In some embodiments, the second therapeutic drug and the compound of formula I or the pharmaceutically acceptable salt thereof may each have the same or different treatment cycles. In some specific embodiments, the second therapeutic drug and the compound of formula I or the pharmaceutically acceptable salt thereof have the same treatment cycle, e.g., a 1-week, 2-week, 3-week or 4-week treatment cycle.

In some specific embodiments, the second therapeutic drug and the compound of formula I or the pharmaceutically acceptable salt thereof have a 3-week treatment cycle.

In some embodiments of the treatment method disclosed herein, epirubicin can be administered to the patient at a dose of 50 mg to 150 mg/m$^2$, for example, at a dose of 50, 54, 60, 72, 80, 90, 100, 110, 120, 135 and/or 150 mg/m$^2$.

Soft Tissue Sarcomas

The soft tissue sarcomas described herein include, but are not limited to: undifferentiated pleomorphic sarcoma (also known as malignant fibrous histiocytoma), angiosarcoma, desmoid tumor, fibrosarcoma, gastrointestinal stromal tumor, Kaposi's sarcoma, leiomyosarcoma, liposarcoma, rhabdomyosarcoma, synovial sarcoma, dermatofibrosarcoma protuberan, nerve sheath tumor, malignant peripheral nerve sheath tumor, alveolar soft-part sarcoma, clear cell sarcoma, malignant mesenchymoma, epithelioid sarcoma, pulmonary alveolar soft-part sarcoma, dedifferentiated liposarcoma, myxoid liposarcoma, pleomorphic liposarcoma, mixed-type liposarcoma, adult fibrosarcoma, low grade fibromyxoid sarcoma, hyalinizing spindle cell tumor, sclerosing epithelioid fibrosarcoma, pericytic (perivascular) tumor, glomus tumor (and variants), glomangiomatosis, malignant glomus tumor, myopericytoma, myofibroma, angioleiomyoma, embryonal rhabdomyosarcoma (including botryoid and anaplastic ones), alveolar rhabdomyosarcoma (including solid and anaplastic ones), pleomorphic rhabdomyosarcoma, spindle cell/sclerosing rhabdomyosarcoma, epithelioid haemangioendothelioma, angiosarcoma of soft tissue, epithelioid malignant peripheral nerve sheath tumor, malignant triton tumour, malignant granular cell tumor, synovial sarcoma NOS, synovial sarcoma (spindle cell), synovial sarcoma (biphasic), clear cell sarcoma of soft tissue, desmoplastic small round cell tumor, extra-renal rhabdoid tumor, neoplasms with perivascular epithelioid cell differentiation (PEComa), intimal sarcoma, undifferentiated/unclassified sarcoma, undifferentiated spindle cell sarcoma, undifferentiated round cell sarcoma, undifferentiated epithelioid cell sarcoma, desmoplastic small round cell tumor, low grade fibromyxoid sarcoma, and borderline soft tissue tumor.

In some specific embodiments, the soft tissue sarcoma is undifferentiated pleomorphic sarcoma, alveolar soft-part sarcoma, angiosarcoma, fibrosarcoma, leiomyosarcoma, liposarcoma, rhabdomyosarcoma, synovial sarcoma, dermatofibrosarcoma protuberan, malignant peripheral nerve sheath tumor, clear cell sarcoma, malignant mesenchymoma, epithelioid sarcoma, undifferentiated sarcoma, and gastrointestinal stromal tumor.

In some specific embodiments, the soft tissue sarcoma is undifferentiated pleomorphic sarcoma.

In some specific embodiments, the soft tissue sarcoma is alveolar soft-part sarcoma.

In the present application, clinical stages of the soft tissue sarcoma include, but are not limited to, locally advanced, and/or advanced (e.g., stage IIIB/IV) and/or metastatic soft tissue sarcomas, wherein, the metastatic soft tissue sarcomas include, but are not limited to, single metastasis, disseminated metastasis and diffuse metastasis of lesions; the metastatic lesions include, but are not limited to, lymph node, pleura, bone, brain, pericardium, adrenal gland and liver lesions. In some embodiments, the soft tissue sarcoma is soft tissue sarcoma with brain metastases. In some embodiments, the pharmaceutical combination is for use in treating a soft tissue sarcoma, wherein the soft tissue sarcoma can be a primary soft tissue sarcoma or a secondary soft tissue sarcoma. In some embodiments, the soft tissue sarcoma is one that has progressed or recurred after being treated with at least one chemotherapy. In some embodiments, the soft tissue sarcoma is one that is intolerant to chemotherapy. In a preferred embodiment, the soft tissue sarcoma is one that has not previously been systemically treated. In some embodiments, the soft tissue sarcoma is undifferentiated pleomorphic sarcoma. In some other specific embodiments, the soft tissue sarcoma is alveolar soft-part sarcoma.

Second Therapeutic Drug

In some embodiments of the present application, the second therapeutic drug includes, but is not limited to, a chemotherapeutic drug, a small molecule targeted anti-tumor drug, and an immunotherapeutic drug.

In some embodiments, the second therapeutic drug is a chemotherapeutic drug, including but not limited to, one or more of a platinum-based drug, a fluoropyrimidine derivative, a camptothecin drug, a taxane drug, a vinca alkaloid drug, an anthracycline drug, an antibiotic, a podophyllum drug, and an antimetabolite drug. Examples that may be listed include, but are not limited to: one or more of a platinum-based drug (e.g., oxaliplatin, cisplatin, carboplatin, miriplatin, nedaplatin, and dicycloplatin), a fluoropyrimidine derivative (e.g., gemcitabine, capecitabine, ancitabine, fluorouracil, difuradin, doxifluridine, tegafur, carmofur, and trifluridine), a taxane drug (e.g., paclitaxel, albumin-bound paclitaxel, and docetaxel), a camptothecin drug (e.g., camptothecin, hydroxycamptothecin, 9-aminocamptothecin, 7-ethylcamptothecin, irinotecan, and topotecan), a vinca alkaloid drug (vinorelbine, vinblastine, vincristine, vindesine, and vinflunine), an anthracycline drug (epirubicin, adriamycin, daunorubicin, pirarubicin, amrubicin, idarubicin, mitoxantrone, aclarubicin, valrubicin, zorubicin, and pixantrone), pemetrexed, carmustine, melphalan, etoposide, teniposide, mitomycin, ifosfamide, cyclophosphamide, azacitidine, methotrexate, bendamustine, liposomal adriamycin, actinomycin D (dactinomycin), bleomycin, pingyangmycin, temozolomide, dacarbazine, peplomycin, eribulin, plinabulin, sapacitabine, treosulfan, 153Sm-EDTMP, tegafur-gimeracil-oteracil potassium, and encequidar.

In some embodiments, the chemotherapeutic drug is one or more selected from the group consisting of adriamycin, epirubicin, daunorubicin, aclacinomycin, actinomycin D, amrubicin, mitomycin, pingyangmycin, pirarubicin, peplomycin, vincristine, cyclophosphamide, ifosfamide, bleomycin, carmustine, etoposide, methotrexate, and cisplatin.

If desired, the second therapeutic drug is used in combination with an ancillary drug for chemotherapy, wherein the ancillary drug for chemotherapy includes, but is not limited to, calcium folinate (CF), leucovorin, mesna, bisphosphonate, amifostine, and hematopoietic cell colony stimulating factors (CSFs). In some embodiments, the ancillary drug for chemotherapy is CF, mesna, or leucovorin.

In some embodiments, the second therapeutic drug is a small molecule targeted anti-tumor drug, including but not limited to protein kinase inhibitors, wherein, the protein kinase inhibitors include, but are not limited to, tyrosine kinase inhibitors, serine and/or threonine kinase inhibitors, and poly ADP-ribose polymerase (PARP) inhibitors; targets of the inhibitors include, but are not limited to, fascin-1 protein, HDAC (histone deacetylase), proteasome, CD38, SLAMF7 (CS1/CD319/CRACC), RANKL, epidermal growth factor receptor (EGFR), anaplastic lymphoma (ALK), MET gene, ROS1 gene, HER2 gene, RET gene, BRAF gene, PI3K signaling pathway, discoidin death receptor 2 (DDR2) gene, fibroblast growth factor receptor 1 (FGFR1), neurotrophic tyrosine kinase type 1 receptor (NTRK1) gene, and KRAS gene; targets of the small molecule targeted anti-tumor drug further include COX-2 (cyclooxygenase-2), APE1 (apurinic apyrimidinic endonuclease), VEGFR (vascular endothelial growth factor receptor), CXCR-4 (chemokine receptor-4), MMP (matrix metalloproteinase), IGF-1R (insulin-like growth factor receptor), Ezrin, PEDF (pigment epithelium derived factor), AS, ES, OPG (osteoprotegerin), Src, IFN, ALCAM (activated leukocyte cell adhesion molecule), HSP, JIP1, GSK-3 (glycogen synthesis kinase 3), CyclinD1 (cell cycle regulatory protein), CDK4 (cyclin-dependent kinase), TIMP1 (tissue inhibitor of metalloproteinase), THBS3, PTHR1 (parathyroid hormone related protein receptor 1), TEM7 (tumor endothelial marker 7), COPS3, and cathepsin K. Examples of the small molecule targeted anti-tumor drug include, but are not limited to, one or more of imatinib, sunitinib, nilotinib, bosutinib, saracatinib, pazopanib, trabectedin, regorafenib, cediranib, bortezomib, panobinostat, carfilzomib, ixazomib, apatinib, erlotinib, afatinib, crizotinib, ceritinib, vemurafenib, dabrafenib, cabozantinib, gefitinib, dacomitinib, osimertinib, alectinib, brigatinib, lorlatinib, trametinib, larotrectinib, icotinib, lapatinib, vandetanib, selumetinib, sorafenib, olmutinib, savolitinib, fruquintinib, entrectinib, dasatinib, ensartinib, lenvatinib, itacitinib, pyrotinib, binimetinib, erdafitinib, axitinib, neratinib, cobimetinib, acalabrutinib, famitinib, masitinib, ibrutinib, rociletinib, nintedanib, lenalidomide, everolimus, LOXO-292, vorolanib, bemcentinib, capmatinib, entrectinib, TAK-931, ALT-803, palbociclib, famitinib L-malate, LTT-462, BLU-667, ningetinib, tipifarnib, poziotinib, DS-1205c, capivasertib, SH-1028, dimethyldiguanide, seliciclib, OSE-2101, APL-101, berzosertib, idelalisib, lerociclib, ceralasertib, PLB-1003, tomivosertib, AST-2818, SKLB-1028, D-0316, LY-3023414, allitinib, MRTX-849, AP-32788, AZD-4205, lifirafenib, vactosertib, mivebresib, napabucasin, sitravatinib, TAS-114, molibresib, CC-223, rivoceranib, CK-101, LXH-254, simotinib, GSK-3368715, TAS-0728, masitinib, tepotinib, HS-10296, AZD-4547, merestinib, olaptesed pegol, galunisertib, ASN-003, gedatolisib, defactinib, lazertinib, CKI-27, S-49076, BPI-9016M, RF-A-089, RMC-4630, AZD-3759, antroquinonol, SAF-189s, AT-101, TTI-101, naputinib, LNP-3794, HH-SCC-244, ASK-120067, CT-707, epitinib succinate, tesevatinib, SPH-1188-11, BPI-15000, copanlisib, niraparib, olaparib, veliparib, talazoparib tosylate, DV-281, siremadlin, telaglenastat, MP-0250, GLG-801, ABTL-0812, bortezomib, tucidinostat, vorinostat, resminostat, epacadostat, tazemetostat, entinostat, mocetinostat and quisinostat, LCL-161, and KML-001. In some embodiments, the small molecule targeted anti-tumor drug is one or more of sorafenib, everolimus, erlotinib, afatinib, crizotinib, ceritinib, vemurafenib, dabrafenib, cabozantinib, gefitinib, dacomitinib, osimertinib, alectinib, brigatinib, lorlatinib, trametinib, larotrectinib, icotinib, lapatinib, vandetanib, selumetinib, olmutinib, savolitinib, fruquintinib, entrectinib, dasatinib, ensartinib, lenvatinib, itacitinib, pyrotinib, binimetinib, erdafitinib, axitinib, neratinib, cobimetinib, acalabrutinib, famitinib, masitinib, ibrutinib, and nintedanib.

In some embodiments, the second therapeutic drug is an immunotherapeutic drug, including but not limited to, one or more of interferons (interferon α, interferon α-1b and interferon α-2b), interleukins, sirolimus, everolimus, ridaforolimus and temsirolimus.

In certain specific embodiments, the second therapeutic drug is one or more of epirubicin, ifosfamide, irinotecan, and adriamycin.

In certain specific embodiments, the second therapeutic drug is epirubicin.

In certain specific embodiments, the second therapeutic drug is one or more, e.g., two, of adriamycin and cyclophosphamide. In a specific embodiment, the second therapeutic drug is an AC regimen (adriamycin+cyclophosphamide).

In certain specific embodiments, the second therapeutic drug is one or more, e.g., one, two, three or four, of cyclophosphamide, vincristine, mesna, and adriamycin. In a specific embodiment, the second therapeutic drug is a VCD regimen (cyclophosphamide+vincristine+mesna+adriamycin).

In certain specific embodiments, the second therapeutic drug is one or two of ifosfamide and mesna.

In a specific embodiment, the second therapeutic drug is an IE regimen (ifosfamide+mesna).

In certain specific embodiments, the second therapeutic drug is one, two or three of cyclophosphamide, adriamycin, and etoposide. In a specific embodiment, the second therapeutic drug is a CAE regimen (cyclophosphamide+adriamycin+etoposide).

In certain specific embodiments, the second therapeutic drug is one or two of adriamycin and dacarbazine. In a specific embodiment, the second therapeutic drug is an AD regimen (adriamycin+dacarbazine).

In certain specific embodiments, the second therapeutic drug is one, two or three of adriamycin, epirubicin, and ifosfamide. In a specific embodiment, the second therapeutic drug is an AIM regimen (adriamycin+ifosfamide).

In certain specific embodiments, the second therapeutic drug is one, two or three of adriamycin, ifosfamide, and dacarbazine. In a specific embodiment, the second therapeutic drug is an MAID regimen (adriamycin+ifosfamide+dacarbazine).

In certain specific embodiments, the second therapeutic drug is one or two of gemcitabine and docetaxel.

Compound of Formula I or Pharmaceutically Acceptable Salt Thereof

The chemical name of the compound of formula I is 1-[[[4-(4-fluoro-2-methyl-1H-indol-5-yl)oxy-6-methoxyquinolin-7-yl]oxy]methyl]cyclopropylamine, which has the following structural formula:

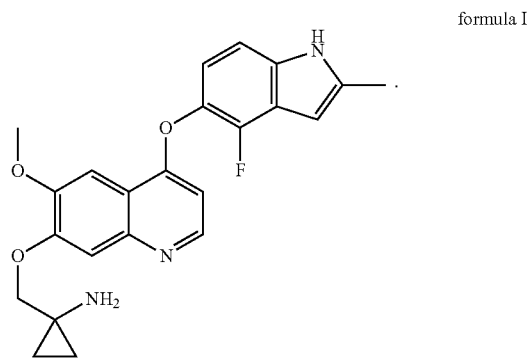 [SMILES: COc1cc2c(Oc3ccc4[nH]c(C)cc4c3F)ccnc2cc1OCC1(N)CC1]

formula I

In the present application, anlotinib refers to the compound of formula I in any case.

The compound of formula I can be administered in its free base form, or in the form of a salt, a hydrate, or a prodrug that may convert in vivo into the free base form. For example, within the scope of the present application, the pharmaceutically acceptable salt of the compound of formula I can be generated from various organic and inorganic acids according to methods commonly known in the art.

In some embodiments, the compound of formula I or the pharmaceutically acceptable salt thereof is administered in the form of a hydrochloride. In some embodiments, the compound of formula I or the pharmaceutically acceptable salt thereof is administered in the form of a monohydrochloride. In some embodiments, the compound of formula I or the pharmaceutically acceptable salt thereof is administered in the form of a dihydrochloride. In some embodiments, the compound of formula I or the pharmaceutically acceptable salt thereof is administered in the form of a crystalline hydrochloride. In specific embodiments, the compound of formula I or the pharmaceutically acceptable salt thereof is administered in the form of a crystalline dihydrochloride.

The compound of formula I or the pharmaceutically acceptable salt thereof and the second therapeutic drug can be administered via multiple routes of administration including, but not limited to, the route selected from the group consisting of oral, parenteral, intraperitoneal, intravenous, intra-arterial, transdermal, sublingual, intramuscular, rectal, transbuccal, intranasal, inhalational, vaginal, intraocular, topical, subcutaneous, intra-adipose, intra-articular and intrathecal administrations. In a specific embodiment, the drug is administered orally.

The amount of the compound of formula I or the pharmaceutically acceptable salt thereof and the second therapeutic drug administered can be determined according to the severity of the disease, the response of the disease, any treatment-related toxicity, and the age and health of a subject. In some embodiments, the daily dose of the compound of formula I or the pharmaceutically acceptable salt thereof is 3 mg to 30 mg. In some embodiments, the daily dose of the compound of formula I or the pharmaceutically acceptable salt thereof is 5 mg to 20 mg. In some embodiments, the daily dose of the compound of formula I or the pharmaceutically acceptable salt thereof is 8 mg to 16 mg. In some embodiments, the daily dose of the compound of formula I or the pharmaceutically acceptable salt thereof is 10 mg to 14 mg. In a specific embodiment, the daily dose of the compound of formula I or the pharmaceutically acceptable salt thereof is 8 mg. In a specific embodiment, the daily dose of the compound of formula I or the pharmaceutically acceptable salt thereof is 10 mg. In a specific embodiment, the daily dose of the compound of formula I or the pharmaceutically acceptable salt thereof is 12 mg. In the present application, for example, for tablets or capsules, "comprising 12 mg of the compound of formula I on a unit dose basis" means that each tablet or capsule ultimately produced comprises 12 mg of the compound of formula I.

The compound of formula I or the pharmaceutically acceptable salt thereof and the second therapeutic drug can be administered once or multiple times daily. In some embodiments, the compound of formula I or the pharmaceutically acceptable salt thereof is administered once daily.

In one embodiment, the compound of formula I or the pharmaceutically acceptable salt thereof is administered once daily in the form of a solid oral preparation.

In the above methods for treatment, the route of administration can be determined according to the activity and toxicity of the drug, the tolerance of the subject, and the like. Preferably, the compound of formula I or the pharmaceutically acceptable salt thereof is administered in an intermittent regimen. The intermittent regimen includes treatment periods and interruption periods. In the treatment period, the compound of formula I or the pharmaceutically acceptable salt thereof can be administered once or multiple times daily. For example, the compound of formula I or the pharmaceutically acceptable salt thereof is administered daily in the treatment period, and then the treatment is interrupted during the interruption period, followed by the treatment period and then the interruption period, over and over again. The ratio of the treatment period to the interruption period in days is 2:0.5 to 2:5, preferably 2:0.5 to 2:3, more preferably 2:0.5 to 2:2, and even more preferably 2:0.5 to 2:1.

In some embodiments, the treatment is administered for 2 consecutive weeks and then interrupted for 2 weeks. In some embodiments, the treatment is administered once daily for 14 consecutive days and then interrupted for 14 days; and then administered once daily for 14 consecutive days and then interrupted for 14 days, etc. Such an intermittent regimen in consecutively 2/2-week treatment/interruption cycle can be repeated multiple times.

In some embodiments, the treatment is administered for 2 consecutive weeks and then interrupted for 1 week. In some embodiments, the treatment is administered once daily for 14 consecutive days and then interrupted for 7 days; and then administered once daily for 14 consecutive days and then interrupted for 7 days, etc. Such an intermittent regimen in consecutively 2/1-week treatment/interruption cycle can be repeated multiple times.

In some embodiments, the treatment is administered for 5 consecutive days and then interrupted for 2 days. In some embodiments, the treatment is administered once daily for 5 consecutive days and then interrupted for 2 days; and then administered once daily for 5 consecutive days and then interrupted for 2 days, etc. Such an intermittent regimen in consecutively 5/2-day treatment/interruption cycle can be repeated multiple times.

In certain specific embodiments, the drug is administered once daily at a dose of 12 mg for 2 consecutive weeks and then interrupted for 1 week.

Pharmaceutical Combination

Each component of the pharmaceutical combination described herein can optionally be used in combination with one or more pharmaceutically acceptable carriers, wherein the components can each independently comprise, or some or all of the components together comprise, a pharmaceutically acceptable carrier and/or an excipient. The components in the pharmaceutical combination described herein can be formulated separately, or some or all of the components are co-formulated. Preferably, the components of the pharmaceutical combination are formulated separately or are each formulated into a suitable pharmaceutical composition. In some embodiment, the pharmaceutical combination disclosed herein can be formulated into a pharmaceutical composition which is suitable for a single dose or multiple doses. In some specific embodiments, the pharmaceutical composition comprising the compound of formula I or the pharmaceutically acceptable salt thereof can be selected from the group consisting of solid pharmaceutical compositions including, but not limited to, tablets or capsules.

The components in the pharmaceutical combination disclosed herein can be administered separately, or some or all of the components are co-administered. The components in the pharmaceutical combination disclosed herein can be administered in a substantially asynchronous manner, or some or all of the components are administered in a substantially synchronous manner.

The components in the pharmaceutical combination disclosed herein can be administered independently, or some or all of the components are co-administered in proper routes including, but not limited to, oral administration or parenteral administration (by intravenous, intramuscular, topical or subcutaneous routes). In some embodiments, the components in the pharmaceutical combination disclosed herein can be administered independently, or some or all of the components are co-administered by oral administration or injection, for example, intravenous injection or intraperitoneal injection.

The components in the pharmaceutical combination disclosed herein can be independent suitable dosage forms, or some or all of the components are co-formulated in a suitable dosage form including, but not limited to, tablet, lozenge, pill, capsule (for example, hard capsule, soft capsule, enteric capsule and microcapsule), elixir, granule, syrup, injection (intramuscular, intravenous and intraperitoneal), granule, emulsion, suspension, solution, dispersant and dosage forms of slow-released preparations for oral or non-oral administration.

In some embodiments of the present application, the pharmaceutical combination is a fixed combination. In some embodiments, the fixed combination is in the form of a solid pharmaceutical composition or a liquid pharmaceutical composition.

In some embodiments of the present application, the pharmaceutical combination is a non-fixed combination. In some embodiments, the second therapeutic drug and the compound of formula I or the pharmaceutically acceptable salt thereof in the non-fixed combination are each in the form of a pharmaceutical composition.

In certain embodiments, the compound of formula I or the pharmaceutically acceptable salt thereof is used in combination with surgical resection and/or radiation therapy.

In some embodiments, the compound of formula I or the pharmaceutically acceptable salt thereof is administered concurrently or sequentially with one or more second therapeutic drugs. In certain embodiments, one or more second therapeutic drugs have been administered to the subject prior to the administration of the compound of formula I or the pharmaceutically acceptable salt thereof, or prior to the combination with the compound of formula I or the pharmaceutically acceptable salt thereof. In certain embodiments, one or more second therapeutic drugs are administered to the subject again after the administration of the compound of formula I or the pharmaceutically acceptable salt thereof, or after the combination with the compound of formula I or the pharmaceutically acceptable salt thereof. In certain embodiments, the compound of formula I or the pharmaceutically acceptable salt thereof has been administered to the subject prior to the administration of one or more second therapeutic drugs, or prior to the combination with one or more second therapeutic drugs. In certain embodiments, the compound of formula I or the pharmaceutically acceptable salt thereof is administered to the subject again after the administration of one or more second therapeutic drugs, or after the combination with one or more second therapeutic drugs. In certain embodiments, one or more second therapeutic drugs are not effective in treating cancer. In some embodiments, the second therapeutic drug is any anti-cancer drug described herein or known in the art.

In some embodiments, the compound of formula I or the pharmaceutically acceptable salt thereof is administered to the subject sequentially after the compound of formula I or the pharmaceutically acceptable salt thereof is administered to the subject in combination with one or more second therapeutic drugs. In some embodiments, the compound of formula I or the pharmaceutically acceptable salt thereof is administered to the subject sequentially orally 2-8 cycles after the compound of formula I or the pharmaceutically acceptable salt thereof is administered to the subject in combination with one or more second therapeutic drugs. In some embodiments, the compound of formula I or the pharmaceutically acceptable salt thereof is administered to the subject sequentially orally 6-24 weeks after the compound of formula I or the pharmaceutically acceptable salt thereof is administered to the subject in combination with one or more second therapeutic drugs. In some embodiments, the compound of formula I or the pharmaceutically acceptable salt thereof is administered to the subject sequentially orally 6 cycles after the compound of formula I or the pharmaceutically acceptable salt thereof is administered to the subject in combination with one or more second therapeutic drugs. In some embodiments, the compound of formula I or the pharmaceutically acceptable salt thereof is administered to the subject sequentially orally 18 weeks after the compound of formula I or the pharmaceutically acceptable salt thereof is administered to the subject in combination with one or more second therapeutic drugs.

In some embodiments, the compound of formula I or the pharmaceutically acceptable salt thereof and the second therapeutic drug are formulated into a preparation that is suitable for oral, parenteral, intraperitoneal, intravenous, intra-arterial, transdermal, sublingual, intramuscular, rectal, transbuccal, intranasal, inhalational, vaginal, intraocular, topical, subcutaneous, intra-adipose, intra-articular and intrathecal administrations, preferably a preparation that is suitable for oral administration, including tablet, capsule, powder, granule, dripping pill, paste and pulvis, and more preferably a tablet or capsule. The tablet may be a common tablet, a dispersible tablet, an effervescent tablet, a sustained-release tablet, a controlled-release tablet or an enteric coated tablet; the capsule may be a common capsule, a sustained-release capsule, a controlled-release capsule or an enteric coated capsule. The oral formulation can be prepared by a conventional method using a pharmaceutically acceptable carrier well known in the art. The pharmaceutically acceptable carrier includes fillers, absorbents, wetting agents, binders, disintegrants, lubricants, and the like. The fillers include starch, lactose, mannitol, microcrystalline cellulose, and the like. The absorbents include calcium sulfate, calcium hydrophosphate, calcium carbonate, and the like. The wetting agents include water, ethanol, and the like. The binders include hydroxypropyl methylcellulose, polyvidone, microcrystalline cellulose, and the like. The disintegrants include croscarmellose sodium, crospovidone, surfactants, low-substituted hydroxypropylcellulose, and the like. The lubricants include magnesium stearate, talcum powder, polyethylene glycol, sodium dodecyl sulfate, silia gel micropowder, and the like. The pharmaceutically acceptable excipient further includes coloring agents, sweeteners and the like.

In some embodiments of the present application, the pharmaceutical combination is a fixed combination. In some embodiments, the fixed combination is in the form of a solid pharmaceutical composition or a liquid pharmaceutical composition.

In some embodiments of the present application, the pharmaceutical combination is a non-fixed combination. In some embodiments, the second therapeutic drug and the compound of formula I or the pharmaceutically acceptable salt thereof in the non-fixed combination are each in the form of a pharmaceutical composition.

In some embodiments, also provided is a kit of a pharmaceutical combination for use in treating a soft tissue sarcoma, comprising (a) a first pharmaceutical composition comprising a chemotherapeutic drug as an active ingredient; and (b) a second pharmaceutical composition comprising the compound of formula I or the pharmaceutically acceptable salt thereof as an active ingredient. In some embodiments, also provided is a kit of a pharmaceutical combination for use in treating a soft tissue sarcoma, comprising (a) a first pharmaceutical composition comprising a small molecule targeted anti-tumor drug as an active ingredient; and (b) a second pharmaceutical composition comprising the compound of formula I or the pharmaceutically acceptable salt thereof as an active ingredient. In some embodiments, also provided is a kit of a pharmaceutical combination for use in treating a soft tissue sarcoma, comprising (a) a first pharmaceutical composition comprising a immunotherapeutic drug as an active ingredient; and (b) a second pharmaceutical composition comprising the compound of formula I or the pharmaceutically acceptable salt thereof as an active ingredient. In some embodiments, also provided is a kit of a pharmaceutical combination for use in treating a soft tissue sarcoma, comprising (a) a first pharmaceutical composition comprising epirubicin as an active ingredient; and (b) a second pharmaceutical composition comprising the compound of formula I or the pharmaceutically acceptable salt thereof as an active ingredient.

Herein, unless otherwise stated, the following terms used in the specification and claims shall have the following meanings for the purposes of the present invention.

In the present application, anlotinib refers to the compound of formula I in any case.

As used herein, the term "treatment failure" refers to the intolerance of toxicity and side effects, disease progression during treatment, or relapse after treatment.

As used herein, the term "subject" means a mammal, such as a rodent, feline, canine, and primate. Preferably, the subject according to the present application is a human.

"Administer", "administration" and "administering" refer to physically introducing the composition comprising a therapeutic agent to an entity using any of a variety of methods and delivery systems known to those skilled in the art. Routes of administration include intravenous, intramuscular, subcutaneous, intraperitoneal, spinal, or other parenteral routes of administration, for example, by injection or infusion. The phrase "parenteral administration" used herein refers to modes of administration apart from enteral and topical administration, typically by injection, including but not limited to, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion and in vivo electroporation. In certain embodiments, the drug is administered via a non-parenteral route. In certain embodiments, the drug is administered orally. Other non-parenteral routes include topical, epidermal or mucosal routes of administration, for example, intranasal, vaginal, rectal, sublingual or topical administration. Administration may also be performed, e.g., once, multiple times, and/or over one or more extended periods of time.

"Entity" includes any human or non-human animal. The term "non-human animal" includes, but is not limited to, vertebrates such as non-human primates, sheep, dogs, and rodents such as mice, rats and guinea pigs. In certain embodiments, the entity is a human. The terms "entity" and "subject" can be used interchangeably herein in certain contexts.

A "therapeutically effective amount" or "therapeutically effective dose" of a drug or therapeutic agent is any amount of a drug that, when used alone or in combination with another therapeutic agent, protects an entity from the onset of a disease or promotes disease regression as evidenced by reduction in the severity of disease symptoms, or increase in the frequency and duration of disease symptom-free stage. The ability of a therapeutic agent to promote disease regression can be evaluated using a variety of methods known to skilled practitioners, such as in a human entity during clinical trials, in an animal model system that predicts efficacy for humans, or by determining the activity of the drug in an in vitro assay.

As an example, an "anti-cancer drug" promotes cancer regression in an entity or prevents further tumor growth. In certain embodiments, the therapeutically effective amount of the drug promotes the cancer regression to the point of eliminating the cancer. "Promoting cancer regression" means that the administration of an effective amount of a drug, alone or in combination with an anti-neoplastic agent results in a reduction of tumor growth or size, necrosis of the tumor, reduction in the severity of at least one disease symptom, or increase in the frequency and duration of disease symptom-free stage. Furthermore, the terms "effective" and "effectiveness" with respect to treatment include pharmacological effectiveness and physiological safety. Pharmacological effectiveness refers to the ability of a drug to promote cancer regression in a subject. Physiological safety refers to the level of toxicity or other adverse physiological effects (adverse effects) at the cellular, organ and/or organism level resulting from drug administration.

As an example for treating a tumor, a therapeutically effective amount of an anti-cancer drug can inhibit cell growth or tumor growth by at least about 10%, at least about 20%, at least about 40%, at least about 60%, or at least about 80% relative to an untreated entity, or, in certain embodiments, relative to a subject treated with standard of care therapy. In other embodiments of the present application, tumor regression may be observed for a period of at least about 20 days, at least about 40 days, or at least about 60 days. Despite these final measurements of therapeutic effectiveness, the evaluation of drugs must also take into account "immune-related" response patterns.

An "immune-related" response pattern refers to the clinical response pattern often observed in cancer subjects treated with an immunotherapeutic agent that produces an anti-tumor effect by inducing a cancer-specific immune response or by altering the innate immune process. This response pattern is characterized by beneficial therapeutic effects following an initial increase in tumor burden or the appearance of new lesions, which would be classified as disease progression and would be synonymous with drug failure in the evaluation of traditional chemotherapeutic agents. Thus, proper evaluation of immunotherapeutic agents may require long-term monitoring of the effect of these agents on target disease.

A "recurrent" cancer is one that regenerates at the initial site or a distant site after being responsive to initial treatment (e.g., surgery). A "locally recurrent" cancer is one that occurs, after treatment, at the same location as the previously treated cancer.

An "unresectable" cancer is one that cannot be removed by surgery.

A "metastatic" cancer refers to one that spreads from one part of the body (e.g., the lung) to another part of the body.

The use of alternatives (e.g., "or") shall be understood to refer to any one, two, or any combination of the alternatives. As used herein, the indefinite articles "a" or "an" shall be understood to mean "one or more" of any listed or enumerated components.

The term "pharmaceutically acceptable" is used herein for those compounds, materials, compositions, and/or dosage forms which are, within the scope of sound medical judgment, suitable for use in contact with the tissues of human beings and animals without excessive toxicity, irritation, allergic response, or other problems or complications, and commensurate with a reasonable benefit/risk ratio.

The term "pharmaceutically acceptable salt" includes salts formed by basic radicals and free acids and salts formed by acidic radicals and free bases, for example, hydrochloride, hydrobromide, nitrate, sulfate, phosphate, formate, acetate, trifluoroacetate, fumarate, oxalate, maleate, citrate, succinate, mesylate, benzenesulfonate and p-methylbenzenesulfonate, preferably, hydrochloride, hydrobromide, sulfate, formate, acetate, trifluoroacetate, fumarate, maleate, mesylate, p-methylbenzenesulfonate, sodium salt, potassium salt, ammonium salt, and amino acid salt, etc. In the present application, when forming a pharmaceutically acceptable salt, the free acid and the basic radical are in a molar ratio of about 1:0.5 to 1:8, preferably 1:0.5, 1:1, 1:2, 1:3, 1:4, 1:5, 1:6, 1:7 or 1:8. In the present application, when forming a pharmaceutically acceptable salt, the free base and the acidic radical are in a molar weight ratio of about 1:0.5 to 1:8, preferably 1:0.5, 1:1, 1:2, 1:3, 1:4, 1:5, 1:6, 1:7 or 1:8.

The term "fixed combination" refers to administration of the active components (for example, a chemotherapeutic drug or the compound of formula I or the pharmaceutically acceptable salt thereof) to a subject simultaneously at a fixed total dose or in a fixed dose proportion, or in the form of a single substance, pharmaceutical composition or formulation.

The term "non-fixed combination" refers to simultaneous, parallel, or sequential and temporally unlimited administration of two or more aforementioned active components as independent substances (for example, a pharmaceutical composition and a formulation) to a subject, wherein the active components administered to the subject reach therapeutically effective amounts. An example, which can be enumerated, of the non-fixed combination is a cocktail therapy, for example, 3 or more active components are administered. In a non-fixed combination, each active component can be packaged, sold or administered as a fully independent pharmaceutical composition. The "non-fixed combination" further includes combined use of "fixed combinations", or a "fixed combination" and an independent substance of any one or more active ingredients.

As used herein, "combination use" or "use in combination" means that two or more active substances may be administered to a subject as a mixture, simultaneously as a single formulation, or sequentially in any order as a single formulation.

The term "pharmaceutical composition" refers to a mixture of one or more active ingredients (e.g. the chemotherapeutic drug or the compound of formula I or the pharmaceutically acceptable salt thereof) or the pharmaceutical combination thereof disclosed herein, and a pharmaceutically acceptable excipient. The pharmaceutical composition is intended to facilitate the administration of the compound or the pharmaceutical combination thereof to a subject.

The term "objective response rate (ORR) in week 18" refers to the percentage of subjects where a complete response (CR) or partial response (PR) obtained by determining the ORR in patients with an advanced soft tissue sarcoma according to RECIST 1.1 is used as the best response.

The term "progression-free survival (PFS)" is defined as the time from the first dose until objective progression or death of the tumor.

The term "overall survival (OS)" is defined as the time from the first dose to death due to any cause. For subjects who are lost to follow-up, the time of the last follow-up is typically regarded as the death time, calculated by days.

The term "safety" refers to the observation of adverse events of combination drug therapy (according to CTCAE V4.0); "CTCAE" refers to the common terminology criteria for adverse events.

The term "disease control rate (DCR)" refers to the disease control rate, including the percentage of cases where complete response, partial response and stable disease have been achieved and sustained over 4 weeks in efficacy-evaluable subjects.

The term "complete response (CR)" means that all target lesions disappear, and the short diameter of all pathological lymph nodes (including target and non-target nodes) must be reduced to <10 mm.

The term "partial response (PR)" means that the sum of the diameters of target lesions is reduced by at least 30% from the baseline level.

The term "progressive disease (PD)" means that the sum of the diameters is relatively increased by at least 20% with reference to the minimum of the sum of the measured diameters of all target lesions throughout the study (or with reference to the baseline if the baseline measurement is minimal).

The term "stable disease (SD)" means that the target lesions are neither sufficiently reduced to level of PR nor sufficiently increased to level of PD, but somewhere in between.

The term "PDX model" refers to a patient-derived tumor xenograft (PDX) model established by directly implanting the tissue from a patient's tumor into an immunodeficient animal.

As used herein, unless otherwise stated, the terms "comprise", "comprises" and "comprising" or equivalents thereof are open-ended statements and mean that elements, components and steps that are not specified may be included in addition to those listed.

All patents, patent applications and other identified publications are expressly incorporated herein by reference for the purpose of description and disclosure. These publications are provided solely because they were disclosed prior to the filing date of the present application. All statements as to the dates of these documents or description as to the contents of these documents are based on the information available to the applicant and do not constitute any admission as to the correctness of the dates of these documents or the content of these documents. Moreover, in any country or region, any reference to these publications herein is not to be construed as an admission that the publications form part of the commonly recognized knowledge in the art.

DETAILED DESCRIPTION

The present application is further described below with reference to specific examples. However, these examples are only illustrative and not intended to limit the scope of the present application. Likewise, the present application is not limited to any particular preferred embodiment described herein. It should be appreciated by those skilled in the art that equivalent substitutions or corresponding modifications for the technical features of the present application still fall with the scope of the present application. Unless otherwise specified, the reagents used in the following examples are commercially available products, and the solutions can be prepared by conventional techniques in the art.

Example 1. Therapeutic Efficacy and Toxicity of Anlotinib in Combination with Epirubicin to Human Sarcoma PDX Model A human sarcoma SA-22-0003PDX nude mouse model was established. The tumor species was derived from the tissue from the excised lesions of clinical malignant fibrous histiocytoma and passaged to the 4th generation via BALB/c nude mice. The sarcoma tissue block (20-30 mm$^3$) from the 4th generation was subcutaneously inoculated in a BALB/c nude mouse to establish a PDX model. On day 24, the subcutaneous tumor tissue of the PDX model grew to about 173 mm$^3$; according to the regimen, the animals were divided into 4 groups (6 nude mice per group): blank control group, anlotinib group (3 mg/kg/d), epirubicin group (2.5 mg/kg), and anlotinib and epirubicin combination group (3.0 mg/kg/d+2.5 mg/kg). Administration route: anlotinib was intragastrically administered daily; epirubicin was injected via the tail vein once every week. The administration was performed for 5 weeks.

The systemic conditions of the animals were observed; the growth of the implanted tumors were determined, and tumor growth curves were plotted. The nude mice were sacrificed after 5 weeks of administration, and biopsy was performed on the whole tumor. Blood was collected to measure the levels of hemoglobin (HGB), albumin (ALB), alanine transaminase (ALT), aspartate transaminase (AST), creatine kinase isoenzyme (CK-MB), cardiac troponin T (cTNT) and B-type N-terminal natriuretic peptide (NT-proBNP); the levels of Ki-67, EGFR, PDGFR-α and PDGFR-β, and the microvessel density (MVD) were measured for the tumors using immunohistochemistry SP method. Cardiac muscle and tumors were observed by HE optical microscopy, and by electron microscopy for ultrastructures.

Results: In the aspect of inhibitory effects on tumors, the average tumor weights for the 4 groups of nude mice are 2.62±0.64 g, 0.71±0.36 g, 1.20±0.42 g, and 0.46±0.20 g, respectively, wherein the anlotinib and epirubicin combination group has a good inhibitory effect on tumors (p<0.05). In the anlotinib and epirubicin combination group, the Ki-67 and EGFR expression rates and the MVD were significantly reduced (p<0.05). In the aspect of safety, the nude mice in the 3 experimental groups were all in good general conditions, which showed no significant difference from those of the control group; no significant difference (p>0.05) in nutritional status (ALB, HBG) was observed between nude mice in all groups, nor did the weight loss exceed 10%. In the aspect of toxicity, compared to those in the control group, the nude mice in the 3 experimental groups suffered certain liver damage (ALT and AST levels increased), but no significant difference (p<0.05) was observed between the 3 experimental groups; in the aspect of cardiac function indices, the NT-proBNP and cTNT levels showed no significant difference (p>0.05) between the groups, and although the CK-MB levels in all experimental groups were improved compared to those in the control group, combination administration did not significantly improve the CK-MB levels (p>0.05). For the nude mice in the 3 experimental groups, no significant damage to the ultrastructures of the cardiac muscle was observed under the electron microscope, which showed no significant difference from those of the control group. For the nude mice in the 3 experimental groups, the HE staining results of the cardiomyocytes showed no significant lesions of each part of the heart.

Conclusions: In the human sarcoma SA-22-0003PDX nude mouse model, the combination use of anlotinib and epirubicin demonstrated a better anti-tumor effect compared to the use of a single drug, and it was well tolerated and showed good safety without causing more severe malnutrition, more damage to the liver and more cardiotoxicity.

Example 2. Clinical Trial of First-Line Treatment of Advanced Soft Tissue Sarcoma with Epirubicin in Combination with Anlotinib Patients who are aged 18-75, diagnosed with locally advanced or metastatic soft tissue sarcoma via histopathology and cannot be operated on were selected to undergone intravenous administration of epirubicin in combination with oral administration of anlotinib. The effectiveness, the safety and the efficacy of the combination therapy were monitored.

Research Endpoints

The primary research endpoint: objective response rate (ORR) in week 18; secondary research endpoints: progression-free survival (PFS), safety, disease control rate (DCR) and overall survival (OS).

Dosage

Anlotinib hydrochloride capsules (anlotinib dihydrochloride as an active ingredient) were orally administered before breakfast at a dose of 12 mg/day (once every day, 1 capsule at a time), with every 3 weeks (21 days) as a cycle; the administration was performed for 2 consecutive weeks and then interrupted for 1 week. If an adverse event occurred, the dosage could be adjusted to 10 mg or 8 mg.

Epirubicin was administered on the first day of each cycle at a dose of 90 mg/m$^2$ through 48 h of continuous intravenous infusion (CIV) (with dexrazoxane used to protect the heart), with every 21 days as a cycle. If an adverse event occurred, the dosage could be adjusted to 80% or 60%.

If the condition, after 6 cycles of combination therapy, was stable, the oral administration of anlotinib (8-12 mg) alone was continued until PD or intolerance occurred.

The dosage was adjusted during the treatment according to adverse events. According to CTCAE V4.0, the dosage was not adjusted when an adverse event of grade 1-2 occurred, and the original regimen was resumed when grade 1 returned; if an adverse event of grade 3-4 occurred, administration was resumed after grade 1 returned. The fact that the adverse event was caused by epirubicin or anlotinib was judged by the researcher, wherein if the event was epirubicin-related, the dosage thereof was reduced to 80%; if the event was anlotinib-related, the dosage thereof was reduced to 10 mg qd; if the event was related to both drugs, the dosages for both drugs were reduced. If an adverse event of grade 3-4 recurred, the dosage could be reduced again according to the judgment of the researcher, with the dosage of epirubicin reduced to 60% and the dosage of anlotinib reduced to 8 mg qd.

This research allowed the use of drugs that were used simply for supportive care and alleviating side effects of chemotherapy (e.g., antiemetics, first-aid medications, drugs for treating AE). The ancillary antiemetic, stomach-protecting and liver-protecting drugs were used according to the routines.

Patient Case

A female, aged 48, had laparoscopic total hysterectomy with bilateral salpingectomy in 2017, and "laparoscopic bilateral ovariectomy+ovarian neoplasm excision+partial greater omentectomy+pelvic adhesiolysis" under general anesthesia in November 2017, and started a 6-cycle GT chemotherapy regimen in December 2017: gemcitabine 1400 mg d1, d8+docetaxel 110 mg d8; clinical diagnosis: connective and soft tissue malignancies (uterine leiomyosarcoma in stage IV), target lesions: the abdominal and pelvic cavities (101 mm at the liver capsule, 104 mm at the pelvic cavity), with a total diameter of 205 mm.

Multiple metastases were found nearly 2 years after uterine leiomyosarcoma excision. The PET/CT results on Jun. 11, 2019 showed that: after multimodality therapy of uterine leiomyosarcoma: 1. with reference to the PET/MRI images, suggestive evidence of multiple metastases in the abdominal and pelvic cavities; 2. multiple gallstones; abdominal and pelvic effusion; 3. probable lymph nodes in the left clavicle area; bilateral pulmonary bronchiectasis with infections; calcification in the left breast. The table below shows the regimen and the efficacy evaluation results.

TABLE 1

| Evaluation Date | Target lesion | Efficacy evaluation |
|---|---|---|
| Regimen for the first cycle: anlotinib 12 mg po qd d1-d14 + epirubicin 140 mg civ 48 h (90 mg/m$^2$), q3w ||| 
| 2019 Jul. 25 | Total diameter of 148 mm (84 mm at the liver capsule, 64 mm at the pelvic cavity) | SD |

TABLE 1-continued

| Evaluation Date | Target lesion | Efficacy evaluation |
|---|---|---|
| Regimen after the beginning of the second cycle: anlotinib 12 mg po qd d1-d14 + epirubicin 110 mg civ 48 h (72 mg/m$^2$), q3w | | |
| 2019 Sep. 5 | Total diameter of 116 mm (63 mm at the liver capsule, 53 mm at the pelvic cavity) | PR |
| 2019 Oct. 17 | Total diameter of 115 mm (59 mm at the liver capsule, 56 mm at the pelvic cavity) | PR |
| 2019 Nov. 28 | Total diameter of 97 mm (47 mm at the liver capsule, 50 mm at the pelvic cavity) | PR |

The efficacy evaluation results show that a total of 25 patients met the criteria, with 13 patients for SD, 1 patient for PR, 9 patients for PD, 1 patient dropping out of the study and 1 patient not efficacy-evaluated, and the DCR was 56%.

According to the content disclosed in the present application, the compositions and methods of the present application have been described in terms of preferred embodiments. However, it will be apparent to those skilled in the art that variations may be applied to the compositions and/or methods and the steps or the sequence of steps of the methods described herein without departing from the concept, spirit and scope of the present application.

The disclosed contents of all documents cited herein are hereby incorporated by reference to the extent that they provide exemplary, procedural and other details supplementary to those described herein.

The invention claimed is:

1. A method for treating a soft tissue sarcoma, comprising administering to a subject in need thereof a therapeutically effective amount of a compound of formula I or a pharmaceutically acceptable salt thereof, and a therapeutically effective amount of epirubicin, formula I

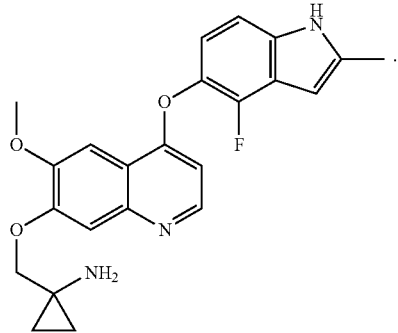

2. The method according to claim 1, wherein the soft tissue sarcoma is selected from undifferentiated sarcoma, angiosarcoma, fibrosarcoma, gastrointestinal stromal tumor, leiomyosarcoma, liposarcoma, rhabdomyosarcoma, synovial sarcoma, dermatofibrosarcoma protuberan, malignant peripheral nerve sheath tumor, alveolar soft-part sarcoma, clear cell sarcoma, malignant mesenchymoma, epithelioid sarcoma.

3. The method according to claim 1, wherein the soft tissue sarcoma is selected from a recurrent soft tissue sarcoma, and/or a metastatic soft tissue sarcoma, and/or a refractory soft tissue sarcoma, and/or an unresectable soft tissue sarcoma, and/or advanced soft tissue sarcoma.

4. The method according to claim 1, wherein the subject has not previously been treated with systemic chemotherapy, and/or the subject has previously been treated with surgery, radiation therapy, induction chemotherapy, concurrent chemotherapy and/or adjuvant chemotherapy, and/or the subject has not previously been treated with systemic chemotherapy but has been treated with surgery, radiation therapy, induction chemotherapy, concurrent chemotherapy and/or adjuvant chemotherapy, and/or the subject has recurrence of disease progression after achieving complete response following surgery, radiation therapy, induction chemotherapy, concurrent chemotherapy and/or adjuvant chemotherapy, and/or the subject has failed to achieve complete response or partial response following surgery, radiation therapy, induction chemotherapy, concurrent chemotherapy and/or adjuvant chemotherapy, and/or the subject with the cancer metastasizes after the entity has been treated with surgery, radiation therapy, induction chemotherapy, concurrent chemotherapy and/or adjuvant chemotherapy.

5. The method according to claim 1, wherein the compound of formula I or the pharmaceutically acceptable salt thereof is administered in an intermittent regimen of alternate treatment and interruption periods; wherein the ratio of the treatment period to the interruption period in days is 2:0.5 to 2:5, 2:0.5 to 2:3, 2:0.5 to 2:2, or 2:0.5 to 2:1; and wherein the intermittent regimen is in one of the following cycles: consecutively 2-week treatment and then 2-week interruption, consecutively 2-week treatment and then 1-week interruption, and consecutively 5-day treatment and then 2-day interruption.

6. The method according to claim 1, wherein the compound of formula I or the pharmaceutically acceptable salt thereof is administered at a daily dose of 3 mg to 30 mg.

7. The method according to claim 1, comprising administering: (i) a pharmaceutical composition at a dose of 6 mg, 8 mg, 10 mg and/or 12 mg of the compound of formula I or the pharmaceutically acceptable salt thereof; and (ii) a pharmaceutical composition at a dose of 50-150 mg/m$^2$ of epirubicin.

8. The method according to claim 1, wherein the soft tissue sarcoma is an undifferentiated pleomorphic sarcoma or alveolar soft-part sarcoma.

9. The method according to claim 1, wherein the soft tissue sarcoma is selected from desmoid tumor, Kaposi's sarcoma, nerve sheath tumor, pulmonary alveolar soft-part sarcoma, dedifferentiated liposarcoma, myxoid liposarcoma, pleomorphic liposarcoma, mixed-type liposarcoma, low grade fibromyxoid sarcoma, hyalinizing spindle cell tumor, sclerosing epithelioid fibrosarcoma, pericytic tumor, *glomus* tumor, glomangiomatosis, myopericytoma, myofibroma, angioleiomyoma, embryonal rhabdomyosarcoma, alveolar rhabdomyosarcoma, pleomorphic rhabdomyosarcoma, spindle cell/sclerosing rhabdomyosarcoma, epithelioid haemangioendothelioma, epithelioid malignant peripheral nerve sheath tumor, malignant triton tumour, malignant granular cell tumor, synovial sarcoma NOS, synovial sarcoma clear cell sarcoma of soft tissue, desmoplastic small round cell tumor, extra-renal rhabdoid tumor, neoplasms with perivascular epithelioid cell differentiation, intimal sarcoma, unclassified sarcoma, undifferentiated spindle cell sarcoma, undifferentiated round cell sarcoma, undifferentiated epithelioid cell sarcoma, desmoplastic small round cell tumor, low grade fibromyxoid sarcoma, and borderline soft tissue tumor.

10. The method according to claim 1, wherein the soft tissue sarcoma is locally advanced soft tissue sarcoma.

\* \* \* \* \*